US005876737A

United States Patent [19]

Schönrock et al.

[11] Patent Number: 5,876,737

[45] Date of Patent: Mar. 2, 1999

[54] USE OF SALICIN AS AN ANTI-IRRITATIVE ACTIVE COMPOUND IN COSMETIC AND TOPICAL DERMATOLOGICAL PREPARATIONS

[75] Inventors: Uwe Schönrock, Nahe; Friedhelm Steckel, Hamburg, both of Germany; Ulrich Kux, Urayasu City; Kazuo Inoue, Naka-Ku, both of Japan

[73] Assignee: Beiersdorf AG, Hamburg, Germany

[21] Appl. No.: 839,619

[22] Filed: Apr. 15, 1997

[30] Foreign Application Priority Data

Apr. 19, 1996 [DE] Germany ........................ 196 15 577.0

[51] Int. Cl.[6] .............................. A61K 6/00; A61K 7/00; A61K 31/74

[52] U.S. Cl. ........................................ 424/401; 424/78.03

[58] Field of Search .............................. 424/78.03, 78.05, 424/485, 445, 486, 487, 401; 514/488, 25, 772.6, 828, 886, 887, 855, 938

[56] References Cited

U.S. PATENT DOCUMENTS

| | | | |
|---|---|---|---|
| 4,764,361 | 8/1988 | Bilski et al. | 424/45 |
| 5,153,000 | 10/1992 | Chikawa et al. | 424/450 |

*Primary Examiner*—Johann Richter
*Assistant Examiner*—Sharon Howard
*Attorney, Agent, or Firm*—Sprung Kramer Schaefer & Briscoe

[57] ABSTRACT

Use of salicin for the cosmetic or dermatological treatment and/or prophylaxis of irritant and/or erythematous skin symptoms.

14 Claims, No Drawings

USE OF SALICIN AS AN ANTI-IRRITATIVE ACTIVE COMPOUND IN COSMETIC AND TOPICAL DERMATOLOGICAL PREPARATIONS

The present invention relates to the use of an active compound known per se for the cosmetic and topical dermatological treatment and/or prophylaxis of erythematous or inflammatory symptoms, in particular dermatosis. The present invention furthermore relates to the use of an active compound known per se for the prevention of irritative or inflammatory skin symptoms when using customary cosmetic or topical dermatological preparations or the use of such an active compound for the reduction of the irritative potential of customary cosmetic or topical dermatological preparations. Moreover, the invention relates to preparations having an extremely low so-called "stinging potential".

The skin, in particular the epidermis, is, as a barrier organ of the human body, subjected to external influences to a particular extent. The epidermis is well-equipped with nerves and peripheroceptors such as Vater-Pacini corpuscles, Merkel cell-neurite complexes and free nerve endings for pain, cold and heat sensation and itching.

In humans with sensitive or easily injured skin, a neurosensory phenomenon described by "stinging" ("to sting"= to wound, smart, to cause pain) can be observed. This "sensitive skin" differs fundamentally from "dry skin" with thickened and indurated horny layers.

Typical reactions of "stinging" in sensitive skin are reddening, tautening and smarting of the skin and also itching.

Itching in atopic skin, and also itching in skin disorders, is to be regarded as a further neurosensory phenomenon.

"Stinging" phenomena can be regarded as disorders to be treated cosmetically. Severe itching, on the other hand, in particular severe itching occurring in atopy, can also be described as a relatively serious dermatological disorder.

Typical, troublesome neurosensory phenomena associated with the terms "stinging" or "sensitive skin" are skin reddening, tingling, prickling, tautening and burning of the skin and itching. They can be caused by stimulating environmental conditions, e.g. massage, surfactant action, influence of the weather such as sun, cold, dryness, but also moist heat, heat radiation and UV radiation, e.g. of the sun.

In the "Journal of the Society of Cosmetic Chemists" 28, pp.197–209 (May 1977), P. J. Frosch and A. M. Kligman describe a method for the estimation of the "stinging potential" of topically administered substances. Positive substances employed here are, for example, lactic acid and pyruvic acid. On measurement according to this method, however, amino acids, in particular glycine, are also determined as having neurosensory activity (such substances are called "stingers").

According to present knowledge, there appears to be an individual difference in sensitivity of this type to very specific substances. This means a person who experiences "stinging effects" on contact with a substance will with high probability experience it repeatedly on any further contact. Contact with other "stingers", however, can just as readily proceed without any reaction. When using some preparations having deodorant or antiperspirant activity, many more-or-less sensitive people have suffered from erythematous skin symptoms.

Erythemas also occur to an increased extent in the nappy area of infants, all the more of babies.

The erythematous action of the ultraviolet part of the sun's radiation on the skin is generally known. While waves having a wave length which is less than 290 nm (the so-called UVC range), are absorbed by the ozone layer in the earth's atmosphere, rays in the range between 290 nm and 320 nm, the so-called UVB range, cause an erythema, a simple sunburn or even more or less severe burns.

A maximum of the erythema activity of sunlight is specified as the relatively narrow range around 308 nm.

Erythematous skin symptoms also occur as concomitant symptoms in certain skin disorders or irregularities. For example, the typical skin rash in the symptoms of acne is regularly more or less severely reddened. In the case of blemished skin, in addition to other influences, bacterial secondary infections are of aetiological importance. One of the most important microorganisms which is connected with blemished skin is Propionibacterium acnes.

Blemished skin and/or comedones adversely affect the well being of the affected persons, however, even in slight cases. Since virtually every juvenile is affected by blemished skin of some intensity or other, there is a need in the case of many people to remedy this condition.

In the case of the complete picture of acne, but also at relatively light intensities, inflammations of the acne pustules frequently result. The prior art was lacking in active compounds which are a satisfactory treatment within the meaning of a cure, but also are a camouflage, i.e. a cosmetic covering of the comedo.

The object of the present invention was thus to find a substance or substance combination active against inflamed comedones.

In about 10% of the population of industrial countries, with a recently increasing tendency, atopy is to be observed, a familial hyper sensitivity of the skin and of the mucous membranes to substances in the environment, with increased readiness to develop hyper sensitivity reactions of the immediate type to substances from the natural environment. Atopy is presumably caused genetically. Atopy can manifest itself as atopic dermatitis.

It was also the object of the present invention to remedy the outlined disadvantages of the prior art.

In particular, it was intended to make available active compounds and preparations comprising such active compounds for the cosmetic and dermatological treatment and/or prophylaxis of erythematous, inflammatory or allergic symptoms, in particular dermatosis, but also of the development of "stinging".

The most frequent types of cosmetic or topically applied dermatological preparations are finely disper sed multiphase systems, in which one or more fat or oil phases are present in addition to one or more water phases. Of these systems, in turn, the actual emulsions are the most widespread.

In simple emulsions, finely disper sed droplets of the second phase (water droplets in w/o or lipid vesicles in o/w emulsions) surrounded by an emulsifier coat are present in one phase. The droplet diameters of the usual emulsions are in the range from about 1 $\mu$m to about 50 $\mu$m. Such "macroemulsions", without further colouring additives, are coloured milky white and opaque. Finer "macroemulsions", whose droplet diameters are in the range from about $10^{-1}$ $\mu$m to about 1 $\mu$m, in turn without colouring additives, are coloured bluish white and opaque. Such "macroemulsions" usually have a high viscosity.

The droplet diameter of microemulsions, on the other hand, is in the range from approximately $10^{-2}$ $\mu$m to approximately $10^{-1}$ $\mu$m. Microemulsions are translucent and usually of low viscosity. The viscosity of many microemulsions of the o/w type, for example, is comparable with that of water.

An advantage of microemulsions is that in the disper se phase active compounds can be present in more finely disper sed form than in the disper se phase of "macroemulsions". A further advantage is that, on account of their low viscosity, they are sprayable. If microemulsions are used as cosmetics, corresponding products are distinguished by high cosmetic elegance.

Per se, the use of the customary cosmetic emulsifiers is innocuous. Nevertheless, emulsifiers, in the end like any chemical substance, can in isolated cases cause allergic reactions or reactions based on hyper sensitivity of the user.

Thus it is known that specific photodermatoses are induced by certain emulsifiers, but also by various fats, and simultaneous exposure to sunlight (e.g. the so-called "Mallorca acne"). Emulsifier-free finely disper sed preparations of an oil and a water phase are customarily not called emulsions, but, depending on the type, hydrodispersions or lipodispersions and have for some time been available to the consumer.

Hydrodispersions are dispersions of a liquid, semi-solid or solid [lacuna] In contrast to o/w emulsions, which are distinguished by a similar phase arrangement, hydrodispersions are essentially free of emulsifiers. Hydrodispersions, incidentally also like emulsions, are metastable systems and are inclined to change into a state of two coherent discrete phases. In emulsions, the choice of a suitable emulsifier prevents phase separation.

With hydrodispersions of a liquid lipid phase in an outer aqueous phase, the stability of such a system can be guaranteed, for example, by building up in the aqueous phase a gel structure, in which the lipid droplets are stably suspended.

W/O lipodispersions, which are the subject of the present invention, are in the reverse analogy emulsifier-free finely disper sed preparations of the water-in-oil type.

Customary, and just recently, increasingly widespread cosmetic and dermatological preparation forms, which can be emulsifier-free but also emulsifier-containing, are gels. In the technical sense gels are understood as meaning: relatively dimensionally stable, easily deformable disper se systems of at least two components which as a rule consist of one—usually solid—colloidally disper sed substance formed of long-chain molecular groups (e.g. gelatin, silicic acid, polysaccharides) as structure-forming agents and a liquid dispersing agent (e.g. water). The colloidally disper sed substance is often described as a thickening or gelling agent. It forms a spatial network in the dispersing agent, it being possible for individual particles present in colloidal form to be more or less firmly linked to one another by means of electrostatic interaction. The dispersing agent, which surrounds the network, is distinguished by electrostatic affinity for the gelling agents, i.e. a predominantly polar (in particular: hydrophilic) gelling agent preferably gels a polar dispersing agent (in particular: water), whereas a predominantly non-polar gelling agent preferably gels non-polar dispersing agents.

Strong electrostatic interactions which are realized, for example, in hydrogening agent bonds between gelling agent and dispersant, but also mutually between dispersing agent molecules, can lead to strong cross-linking even of the dispersing agent. Hydrogels can consist almost to 100% of water (besides, for example, about 0.2–1.0% of a gelling agent) and at the same time have absolutely solid consistency. The water content is in this case present in ice-like structural elements, so that gels are therefore absolutely justified in the derivation of their name [from the latin "gelatum"="congelation" via the alchemistic expression "gelatina" (16th Century) for current German "Gelatine"].

In cosmetic and pharmaceutical formulation, lipogels and oleogels (from waxes, fats and fatty oils) and also carbogels (from paraffin or petrolatum) are also familiar. In practice, a differentiation is made between oleogels, which are virtually water-free, and hydrogels, which are virtually fat-free. Usually, gels are transparent. In cosmetic or pharmaceutical formulation, gels are generally distinguished by semi-solid, often fluid consistency.

Cosmetic sticks, in particular lipsticks, preferably lipcare sticks, but also deodorant sticks are also customary preparations.

The skin of the lips has only an extremely thin horny layer. Sweat glands are hardly to be found on the lips at all, and sebaceous glands only sporadically. The skin of the lips is therefore virtually free of fats and tends, particularly in cold and dry weather, to dry out. During the course of this small cracks can form in the skin, and the sensitivity of the lips to chemical, physical and microbial effects (e.g. food, sunlight, herpes simplex viruses) increases.

To prevent this is the object of lipcare sticks. These products mostly contain too high a content of waxes and fatty components which after application form a covering layer over the lips.

Looked at technically, almost all lipsticks are water-free fatty mixtures of solid or semi-solid waxes and liquid oils, the highly purified paraffin oils and waxes being the lipstick base.

According to the ideal requirement profile, lipsticks should be able to be applied smoothly and without great frictional resistance. Additionally, a lipstick should impart to the lips even on slight pressure a fatty film which is not smeary, dull or tacky, but nevertheless well-adhering. As a result of this fatty film the lips should then be rendered smooth and supple.

In the preparations for lipcare sticks, it is additionally possible to incorporate active compounds which are useful for lipcare or lip protection, e.g. vitamins, moisture-providing agents, sunscreens, covering pigments, etc.

A main disadvantage of the prior art, however, is that the incorporation of the active compound useful for lipcare, i.e. substances active against irritant and/or erythematous skin conditions, into the bases of cosmetic sticks, be it for lipcare or the deodorants field, is extremely problematical or in isolated cases was impossible.

An object of the present invention was thus furthermore to find substances active against irritant and/or erythematous skin conditions which can be incorporated in all abovementioned (but also in optionally unmentioned customary) cosmetic or topical dermatological presentation forms, and/or which decrease the irritation potential of the abovementioned (but also optionally unmentioned customary) cosmetic or topical dermatological presentation forms.

Salicin, hereafter also called "the active compound used according to the invention", displays anti-irritant, in particular anti-inflammatory and anti-erythematous action.

Salicin, also 2-hydroxymethylphenyl β-D-glucopyranoside or saligenin-β-glucoside is contained in the bark of willows and poplars to about 7%. Salicin is distinguished by the chemical structure.

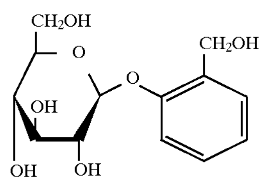

Since antiquity, it has been known that willow and poplar bark have antipyretic properties (entry "Salicin", Römpp Chemie Lexikon Volume 5, Georg Thieme Verlag Stuttgart, New York, 9th Edition, 1992). Nevertheless, it was not possible for the person skilled in the art to assume that it was possible to make available salicin successfully for use in cosmetic and topical dermatological preparations.

Surprisingly, the use of salicin for the cosmetic or dermatological treatment and/or prophylaxis of irritant and/or erythematous skin symptoms remedies the disadvantages of the prior art.

The present invention is particularly embodied by the use of salicin for the cosmetic or dermatological treatment and/or prophylaxis of irritant and/or erythematous skin symptoms, in particular the use for the control and prophylaxis of the erythematous skin symptoms in blemished skin or acne vulgaris, in particular in inflamed comedones, in reddened skin of infants in the nappy area, in inflamed skin around the mouth and nose area, in herpes labialis, in sunburn, and in slight skin fissures. The present invention is furthermore embodied by the use of salicin for the control and prophylaxis of so-called "stinging", the use of salicin for the treatment of atopic dermatitis, skin allergies of type I and type IV, and the use of salicin for increasing the irritancy threshold in sensitive skin.

According to the invention, the content of salicin in the cosmetic or topical dermatological preparations can be 0.01–10% by weight, preferably 0.1–5% by weight, in particular 0.2–2.0% by weight, based on the total weight of the preparations.

It has a surprisingly emerged that the active compound used according to the invention fulfils the objects underlying the invention. When used according to the invention, it is even fundamentally possible to select preparations and active compounds, auxiliaries and additives customary for this purpose which per se are not particularly mild, since their possible irritant, for example erythema-promoting, action on particularly sensitive people can be compensated by the active compound used according to the invention.

This property makes the active compound used according to the invention particularly suitable as a secondary constituent of cosmetics or topical dermatics which provides relief in applications in which skin irritation is almost unavoidable. An example of such applications is the cosmetic or medicinal treatment of blemished skin or acne vulgaris, in which erythematous skin symptoms regularly occur as a side effect.

A particularly advantageous embodiment is therefore regarded as the use of salicin for the control and prophylaxis of the erythematous skin symptoms in blemished skin or acne vulgaris.

It may be stressed that the subject of the present teaching is in no way intended to encourage the unhesitating use of raw materials which are dubious for health reasons. On the contrary, the present teaching relates to the extension of the possibilities of use of some substances which are harmless per se to people having a sensitive reaction to these substances in spite of everything.

Advantageously, the active compound used according to the invention can be incorporated into customary cosmetic and dermatological preparations, which can be present in various forms. They can thus be, for example, a solution, an emulsion of the water-in-oil (w/o) type or of the oil-in-water (o/w) type, or a multiple emulsion, for example of the water-in-oil-in-water (w/o/w) type or oil-in-water-in-oil (o/w/o) type, a hydrodispersion or lipodispersion, a gel, a solid stick or even an aerosol.

Emulsions according to the invention within the meaning of the present invention, e.g. in the form of a protective skin cream, of a skin lotion or of a cosmetic milk, for example in the form of a sunscreen cream or a sunscreen milk, are advantageous and contain, for example, fats, oils, waxes and/or other fatty materials, as well as water and one or more emulsifiers, such as are customarily used for a formulation of this type.

It is also possible and advantageous within the meaning of the present invention to add the active compound used according to the invention to aqueous systems or surfactant preparations for cleaning the skin and the hair.

It is of course known to the person skilled in the art that demanding cosmetic compositions are usually inconceivable without the customary auxiliaries and additives. Among these are included, for example, consistency-imparting agents, fillers, perfume, colorants, emulsifiers, additional active compounds such as vitamins or proteins, sunscreens, stabilisers, insect repellents, alcohol, water, salts, substances having antimicrobial, proteolytic or keratolytic activity, etc.

The corresponding requirements apply mutatis mutandis to the formulation of medicinal preparations.

Medicinal topical compositions within the meaning of the present invention as a rule contain one or more medicaments in an efficacious concentration. For the sake of simplicity, for clearer differentiation between cosmetic and medicinal use and appropriate products refer to the legal requirements of the Federal Republic of Germanyl (e.g. Cosmetics Regulations, Food and Drugs Act).

It is likewise advantageous in this case to add the active compound used according to the invention as an additive to preparations which already contain other active compounds for other purposes.

Accordingly, cosmetic or topical dermatological compositions within the meaning of the present invention can, for example, be used, depending on their composition, as skin protection cream, cleansing milk, sunscreen lotion, nourishing cream, day or night cream, etc. It is optionally possible and advantageous to use the compositions according to the invention as a base for pharmaceutical formulations.

In particular, the active compound used according to the invention can be used as an additive in cosmetic deodorants or antiperspirants. Agents having deodorant or antiperspirant activity which can be used are then the customary substances known to the person skilled in the art. For example, by means of astringents—mainly aluminium salts such as aluminium hydroxychloride—the formation of perspiration can be suppressed.

By the use of antimicrobial substances in cosmetic deodorants the bacterial flora on the skin can be reduced. At the same time, in the ideal case only the odour-causing microorganisms in the skin should be effectively reduced. Monocarboxylic acid esters of di- or triglycerol, for example, are advantageous. However, other substances having antimicrobial activity are also suitable.

According to the invention, even the use of deodorant active compounds which are not particularly mild per se or act as antiperspirants is possible and may be advantageous, since their possible erythema-promoting action can be compensated by the active compound used according to the invention.

Cosmetic and dermatological preparations also convenient for the purpose of the present invention are those in the form of a sunscreen. Besides the active compound used according to the invention, these preferably additionally contain at least one UVA filter substance and/or at least one UVB filter substance and/or at least one inorganic pigment.

However, it is also advantageous within the meaning of the present invention to make available those cosmetic and dermatological preparations whose main purpose is not protection from sunlight, but which nevertheless contain UV-protective substances. Thus UV-A and UV-B filter substances are usually incorporated, for example, in day creams.

Advantageously, preparations according to the invention contain substances which absorb UV radiation in the UVB range, the total amount of the filter substances being, for example, 0.1% by weight to 30% by weight, preferably 0.5 to 10% by weight, in particular 1 to 6% by weight, based on the total weight of the preparations.

The UVB filters can be oil-soluble or water-soluble. Oil-soluble substances which may be mentioned are, for example:

3-benzylidenecamphor and its derivatives, e.g. 3-(4-methylbenzylidene)camphor 4-aminobenzoic acid derivatives, preferably 2-ethylhexyl 4-dimethylaminobenzoate, amyl 4-dimethylaminobenzoate;

esters of cinnamic acid, preferably 2-ethylhexyl 4-methoxycinnamate, isopentyl 4-methoxycinnamate;

esters of salicylic acid, preferably 2-ethylhexyl salicylate, 4-isopropylbenzyl salicylate, homomenthyl salicylate;

derivatives of benzophenone, preferably 2-hydroxy-4-methoxybenzophenone, 2-hydroxy-4-methoxy-4'methylbenzophenone, 2,2'-dihydroxy-4-methoxybenzophenone;

esters of benzylidenemalonic acid, preferably di(2-ethylhexyl) 4-methoxybenzylidenemalonates;

2,4,6-trianilino(p-carbo-2'-ethyl-1'-hexyloxy)-1,3,5-triazine

Advantageous water-soluble substances are:

2-phenylbenzimadazole-5-sulphonic acid and its salts, e.g. sodium, potassium or triethanolammonium salts, sulphonic acid derivatives of benzophenones, preferably 2-hydroxy-4-methoxybenzophenone-5-sulphonic acid and its salts;

sulphonic acid derivatives of 3-benzylidenecamphor, such as, for example, 4-(2-oxo-3-bornylidenemethyl)-benzenesulphonic acid, 2-methyl-5-(2-oxo-3-bornylidnemethyl)sulphonic acid and their salts.

The list of UVB filters mentioned which can be used according to the invention is of course not intended to be limiting.

The invention also relates to the combination of a UVA filter according to the invention with a UVB filter or a cosmetic or dermatological preparation according to the invention which also contains a UVB filter.

It may also be advantageous to employ in preparations according to the invention UVA filters which are customarily contained in cosmetic and/or dermatological preparations. Such filter substances are preferably derivatives of dibenzoylmethane, in particular 1-(4'-tert-butylphenol)-3-(4'-methoxyphenyl)propane-1,3-dione and 1-phenyl-3-(4'-isopropylphenyl)propane-1,3-dione. Preparations which contain these combinations are also a subject of the invention. The same amounts of UVA filter substances can be used which were mentioned for UVB filter substances.

Cosmetic and/or dermatological preparations within the meaning of the present invention can also contain inorganic pigments which are customarily used in cosmetics for the protection of the skin from UV rays. These are oxides of titanium, zinc, iron, zirconium, silicon, manganese, aluminium, cerium and mixtures thereof, as well as modifications in which the oxides are the active agents. They are particularly preferably pigments based on titanium dioxide. The amounts mentioned for the above combinations can be used.

The cosmetic and dermatological preparations according to the invention can contain cosmetic active compounds, auxiliaries and/or additives such as are customarily used in such preparations, e.g. antioxidants, preservatives, bactericides, perfumes, substances for preventing foaming, colorants, pigments which have a colouring action, thickeners, surface-active substances, emulsifiers, emollients, moisturising and/or moisture-retaining substances, fats, oils, waxes or other customary constituents of a cosmetic or dermatological formulation such as alcohols, polyols, polymers, foam stabilisers, electrolytes, organic solvents or silicone derivatives.

It is advantageous to add to the preparations within the meaning of the present invention further anti-irritants or anti-inflammatory active compounds, in particular batyl alcohol (a-octadecyl glyceryl ether), selachyl alcohol (α-9-octadecenyl glyceryl ether), chimyl alcohol(α-hexadecyl glyceryl ether), bisabolol and/or panthenol.

It is also advantageous to add to the preparations within the meaning of the present invention customary antioxidants. According to the invention, convenient antioxidants which can be used are all antioxidants suitable or utilisable for cosmetic and/or dermatological applications.

Advantageously, the antioxidants are selected from the group consisting of amino acids (e.g. glycine, histidine, tyrosine, tryptophan) and their derivatives, imidazoles (e.g. urocanic acid) and its derivatives, peptides such as D,L-carnosine, D-carnosine, L-carnosine and their derivatives (e.g. anserine), carotenoids, carotenes (e.g. α-carotene, β-carotene, lycopene) and their derivatives, lipoic acid and its derivatives (e.g. dihydrolipoic acid), aurothioglucose, propylthiouracil and other thiols (e.g. thioredoxin, glutathione, cysteine, cystine, cystamine and their glycosyl, N-acetyl, methyl, ethyl, propyl, amyl, butyl and lauryl, palmitoyl, oleyl, γ-linoleyl, cholesteryl and glyceryl esters) and also their salts, dilauryl thiodipropionate, distearyl thiodipropionate, thiodipropionic acid and its derivatives (esters, ethers, peptides, lipids, nucleotides, nucleosides and salts) and also sulphoximine compounds (e.g. buthionine sulphoximine, homocysteine sulphoximine, buthionine sulphone, penta-,hexa- and heptathionine sulphoximine) in very low tolerable doses (e.g. pmol to μmol/kg), furthermore (metal) chelators (e.g. α-hydroxy fatty acids, palmitic acids, phytic acid, lactoferrin), α-hydroxy acids (e.g. citric acid, lactic acid, maleic acid), humic acid, bile acid, bile extracts, bilirubin, biliverdin, EDTA, EGTA and their derivatives, unsaturated fatty acids and their derivatives (e.g. γ-linolenic acid, linoleic acid, oleic acid), folic acid and its derivatives, ubiquinone and ubiquinol and their derivatives, vitamin C and derivatives (e.g. ascorbyl palmitate, Mg- ascorbyl phosphate, ascorbyl acetate), tocopherols and derivatives (e.g. vitamin E acetate) and also coniferyl benzoate of gum benzoin, rutic acid and its derivatives, ferulic acid and its derivatives, butylhydroxytoluene,butylhydroxyanisole, nordihydroguaiaretic acid, trihydroxybutyrophenone, uric acid and its derivatives, mannose and its derivatives, zinc and its derivatives (e.g. ZnO, $ZnSO_4$), selenium and its derivatives (e.g. selenomethionine), stilbene and its derivatives (e.g. stilbene oxide, trans-stilbene oxide) and the derivatives suitable according to the invention (salts, esters, ethers, sugars, nucleotides, nucleosides, peptides and lipids) of the active compounds mentioned.

The amount of the antioxidants (one or more compounds) in the preparations is preferably 0.001 to 30% by weight, particularly preferably 0.05–20% by weight, in particular 1–10% by weight, based on the total weight of the preparation.

If vitamin E and/or its derivatives is/are the antioxidant (s), it is advantageous to select the respective concentrations thereof from the range from 0.001 to 10% by weight, based on the total weight of the formulation.

If the cosmetic or dermatological preparation within the meaning of the present invention is a solution or emulsion or dispersion, the following can be used as solvents:

- water or aqueous solutions
- oils, such as triglycerides of capric or of caprylic acid, but preferably castor oil;
- fats, waxes and other natural and synthetic fatty materials, preferably esters of fatty acids with alcohols of low C number, e.g. with isopropanol, propylene glycol or glycerol, or esters of fatty alcohols with alkanoic acids of low C number or with fatty acids;
- alcohols, dioles or polyoles of low C number, and also their ethers, preferably ethanol, isopropanol, propylene glycol, glycerol, ethylene glycol, ethylene glycol monoethyl or monobutyl ether, propylene glycol monomethyl, monoethyl or monobutyl ether, diethylene glycol monomethyl or monoethyl ether and analogous products.

In particular, mixtures of the abovementioned solvents are used. In the case of alcoholic solvents water can be a further constituent.

The oil phase of the emulsions, oleogels or hydrodispersions or lipodispersions within the meaning of the present invention is advantageously selected from the group consisting of the esters of saturated and/or unsaturated, branched and/or unbranched alkanecarboxylic acids of a chain length of 3 to 30 C atoms and saturated and/or unsaturated, branched and/or unbranched alcohols of a chain length of 3 to 30 C atoms, from the group consisting of the esters of aromatic carboxylic acids and saturated and/or unsaturated, branched and/or unbranched alcohols of a chain length of 3 to 30 C atoms. Such ester oils can then advantageously be selected from the group consisting of isopropyl myristate, isopropyl palmitate, isopropyl stearate, isopropyl oleate, n-butyl stearate, n-hexyl laurate, n-decyl oleate, isooctyl stearate, isononyl stearate, isononyl isononanoate, 2-ethylhexyl palmitate, 2-ethylhexyl laurate, 2-hexyldecyl stearate, 2-octyldodecyl palmitate, oleyl oleate, oleyl erucate, erucyl oleate, erucyl erucate and also synthetic, semisynthetic and natural mixtures of such esters, e.g. jojoba oil.

Furthermore, the oil phase can advantageously be selected from the group consisting of the branched and unbranched hydrocarbons and hydrocarbon waxes, the silicone oils, the dialkyl ethers, the group consisting of the saturated or unsaturated, branched or unbranched alcohols, and also the fatty acid triglycerides, namely the triglycerol esters of saturated and/or unsaturated, branched and/or unbranched alkanecarboxylic acids of a chain length of 8 to 24, in particular 12–18, C atoms. The fatty acid triglycerides can, for example, be advantageously selected from the group consisting of the synthetic, semisynthetic and natural oils, e.g. olive oil, sunflower oil, soya bean oil, ground nut oil, rape seed oil, almond oil, palm oil, coconut oil, palm kernel oil and the like.

Any desired mixtures of such oil and wax components can also advantageously be employed within the meaning of the present invention. It may also optionally be advantageous to employ waxes, for example cetyl palmitate, as the sole lipid component of the oil phase.

Advantageously, the oil phase is selected from the group consisting of 2-ethylhexyl isostearate, octyldodecanol, isotridecyl isononanoate, isoeicosane, 2-ethylhexyl cocoate, $C_{12-15}$-alkyl benzoate, caprylic-capric acid triglyceride, dicaprylyl ether.

Mixtures of $C_{12-15}$-alkyl benzoate and 2-ethylhexyl isostearate, mixtures of $C_{12-15}$-alkyl benzoate and isotridecyl isononanoate, and mixture of $C_{12-15}$-alkyl benzoate, 2-ethylhexyl isostearate and isotridecyl isononanoate are particularly advantageous.

Of the hydrocarbons, paraffin oil, squalane and squalene can advantageously be used within the meaning of the present invention.

Advantageously, the oil phase can furthermore contain cyclic or linear silicone oils or consist completely of such oils, it being preferred, however, to use an additional amount of other oil phase components apart from the silicone oil or the silicone oils.

Advantageously, cyclomethicone (octamethylcyclotetrasiloxane) is employed as the silicone oil to be used according to the invention. However, other silicone oils can also be advantageously used within the meaning of the present invention, for example hexamethylcyclotrisiloxane, polydimethylsiloxane and poly (methylphenylsiloxane).

Furthermore, mixtures of cyclomethicone and isotridecyl isononanoate, and of cyclomethicone and 2-ethylhexyl isostearate, are particularly advantageous.

Gels used according to the invention customarily contain alcohols of low C number, e.g. ethanol, isopropanol, 1,2-propanediol, glycerol and water or an abovementioned oil in the presence of a thickening agent which in the case of oily-alcoholic gels is preferably silica or an aluminium silicate, and in the case of aqueous-alcoholic or alcoholic gels is preferably a polyacrylate.

Solid sticks contain, for example, natural or synthetic waxes, fatty alcohols or fatty acid esters. Lipcare sticks and stick formulations for body deodorisation are preferred.

Customary bases which are suitable for use as cosmetic sticks within the meaning of the present invention are liquid oils (e.g. paraffin oils, castor oil, isopropyl myristate), semi-solid constituents (e.g. petroleum jelly, lanolin), solid constituents (e.g. beeswax, ceresin and microcrystalline waxes or ozocerite) and also high-melting waxes (e.g. carnauba wax, candelilla wax).

Suitable propellants for cosmetic and/or dermatological preparations within the meaning of the present invention, which can be sprayed from aerosol containers are the customary known easily volatile, liquefied propellants, for example hydrocarbons (propane, butane, isobutane), which can be employed on their own or as a mixture. Compressed air can also be advantageously used.

Of course, the person skilled in the art knows that there are non-toxic propellant gases which would be fundamentally suitable for the realization of the present invention in the form of aerosol preparations, but which nevertheless should be dispensed with because of dubious effects on the environment or other concomitant circumstances, in particular fluorohydrocarbons and chlorofluorocarbons (CFCs).

Cosmetic and dermatological preparations within the meaning of the present invention for cleaning the skin or hair are, for example, shampoos. Bath, shower and hand-washing preparations are also advantageous embodiments of the present invention.

Furthermore, preparations within the meaning of the present invention for use on the hair can also be those preparations which are used when rinsing the hair before or after shampooing, before or after permanent wave treatment, or before or after dyeing or bleaching hair, preparations for hot-air drying or setting of the hair, preparations for dyeing or bleaching, a hairdressing and treatment lotion, a hair lacquer or permanent wave composition.

Cosmetic preparations within the meaning of the present invention which are a skin cleansing agent or shampoo preferably contain at least one surface-active substance, or alternatively mixtures of such substances, selected from the group consisting of the anionic, cationic, non-ionic and/or amphoteric surfactants, for example conventional soaps, e.g. fatty acid salts of sodium, alkyl sulphates, alkyl ether sulphates, alkane- and alkylbenzenesulphonates, sulphoacetates, sulphobetaines, sarcosinates, amidosulphobetaines, sulphosuccinates, sulphosuccinic acid monoesters, alkyl ether carboxylates, protein-fatty acid condensates, alkylbetaines and amidobetaines, fatty acid alkanolamides and/or polyglycol ether derivatives, an effective amount of active compound according to the invention, and optionally auxiliaries, such as are customarily used for this purpose.

The surface-active substance or the mixtures of these substances can be present in the skin cleansing agent or shampoo in a concentration of between 1% by weight and 50% by weight.

If the cosmetic or dermatological preparations within the meaning of the present invention are present in the form of a lotion which is rinsed out and is applied, for example, before or after bleaching, before or after shampooing, between two shampooing steps, or before or after permanent wave treatment, we are dealing here, for example, with aqueous or aqueous-alcoholic solutions which optionally contain surface-active substances, preferably non-ionic or cationic surface-active substances whose concentration can be between 0.1 and 10% by weight, preferably between 0.2 and 5% by weight. These cosmetic and/or dermatological preparations can also be aerosols containing the auxiliaries customarily used for this purpose.

A cosmetic preparation in the form of a lotion within the meaning of the present invention, which is not rinsed out, in particular a lotion for setting the hair, a lotion which is used when hot-air drying the hair, a hairdressing and treatment lotion, is in general an aqueous, alcoholic or aqueous-alcoholic solution and contains at least one cationic, anionic, non-ionic or amphoteric polymer or alternatively mixtures thereof, and also the active compound combinations according to the invention. The amount of the polymer used is, for example, between 0.1 and 10% by weight, preferably between 0.1 and 3% by weight.

Cosmetic preparations within the meaning of the present invention for the treatment and care of the hair, which contain the active compound used according to the invention, can be present as emulsions which are of the non-ionic or anionic type. Besides water, non-ionic emulsions contain oils or fatty alcohols which, for example, can also be polyethoxylated or polypropoxylated, or alternatively mixtures of both organic components. These emulsions optionally contain cationic surface-active substances.

Cosmetic preparations within the meaning of the present invention for the treatment and care of the hair can be present as gels which, besides an effective content of active compound according to the invention and solvents customarily used for this purpose, preferably water, additionally contain organic thickening agents, e.g. gum arabic, xanthan gum, sodium alginate, cellulose derivatives, preferably methylcellulose, hydroxymethylcellulose, hydroxyethylcellulose, hydroxypropylcellulose, hydroxypropylmethylcellulose or inorganic thickening agents, e.g. aluminium silicates such as, for example, bentonite, or a mixture of polyethylene glycol and polyethylene glycol stearate or distearate. The thickening agent is contained in the gel, for example, in an amount between 0.1 and 30% by weight, preferably between 0.5 and 15% by weight.

The following examples are intended to explain the present invention.

Example 1

| W/O cream | % by weight |
|---|---|
| Paraffin oil (GP 9) | 10.00 |
| Petrolatum | 4.00 |
| Wool wax alcohol | 1.00 |
| PEG-7 hydrogenated castor oil | 3.00 |
| Aluminium stearate | 0.40 |
| Salicin | 0.50 |
| Glycerol | 2.00 |
| Preservative, colorants, perfume | q.s |
| Water | to 100.00 |

Example 2

| W/O lotion | % by weight |
|---|---|
| Paraffin oil (GP 9) | 20.00 |
| Petrolatum | 4.00 |
| Glucose sesquiisostearate | 2.00 |
| Aluminium stearate | 0.40 |
| Salicin | 0.50 |
| α-tocopheryl acetate | 1.00 |
| Glycerol | 5.00 |
| Preservative, colorants, perfume | q.s. |
| Water | to 100.00 |

Example 3

| O/W lotion | % by weight |
|---|---|
| Paraffin oil (GP 9) | 8.00 |
| Isopropyl palmitate | 3.00 |
| Petrolatum | 4.00 |
| Cetylstearyl alcohol | 2.00 |
| PEG 40 castor oil | 0.50 |
| Sodium cetylstearyl sulphate | 0.50 |
| Sodium carbomer | 0.40 |
| Salicin | 0.50 |
| Glycerol | 3.00 |
| α-tocopherol | 0.20 |
| Octyl methoxycinnamate | 5.00 |
| Butylmethoxydibenzoylmethane | 1.00 |
| Preservative, colorants, perfume | q.s. |
| Water | to 100.00 |

Example 4

| O/W cream | % by weight |
|---|---|
| Paraffin oil (GP 9) | 7.00 |
| Avocado oil | 4.00 |
| Glyceryl monostearate | 2.00 |
| Salicin | 0.50 |
| Titanium dioxide | 1.00 |
| Sodium lactate | 3.00 |
| Glycerol | 3.00 |
| Preservative, colorants, perfume | q.s. |
| Water | to 100.00 |

-continued

Example 5

| Lipcare stick | % by weight |
|---|---|
| Hydrogenated castor oil | 4.00 |
| Ceresin | 8.00 |
| Beeswax | 4.00 |
| Carnauba wax | 2.00 |
| Petrolatum | 40.00 |
| Salicin | 0.50 |
| β-carotene | 0.10 |
| Preservative, colorants, perfume | q.s. |
| Paraffin oil | to 100.00 |

Example 6

| Lipcare stick | % by weight |
|---|---|
| Isopropyl lanolate | 10.00 |
| Acetylated lanolin | 4.00 |
| Beeswax, bleached | 9.00 |
| Carnauba wax | 4.00 |
| Petrolatum | 40.00 |
| Salicin | 0.50 |
| α-tocopherol acetate | 0.10 |
| Preservative, colorants, perfume | q.s. |
| Paraffin oil | to 100.00 |

Example 7

| Liposome-containing gel | % by weight |
|---|---|
| Lecithin | 6.00 |
| Shea butter | 3.00 |
| Salicin | 0.50 |
| α-tocopherol | 0.20 |
| Biotin | 0.08 |
| Sodium citrate | 0.50 |
| Glycine | 0.20 |
| Urea | 0.20 |
| Sodium PCA | 0.50 |
| Hydrolysed collagen | 2.00 |
| Xanthan gum | 1.40 |
| Sorbitol | 3.00 |
| Preservative, colorants, perfume | q.s. |
| Water | to 100.00 |

Example 8

| Gel | % by weight |
|---|---|
| Carbopol 934 P | 2.00 |
| Triethanolamine | 3.00 |
| Salicin | 0.50 |
| α-tocopherol acetate | 0.20 |
| Polyoxyethylene sorbitan fatty acid ester (Tween 20) | 0.50 |
| Glycerol | 2.00 |
| Sodium PCA | 0.50 |
| Hydrolysed collagen | 2.00 |
| Preservative, colorants, perfume | q.s. |
| Water | to 100.00 |

Example 9

| Sunscreen emulsion | % by weight |
|---|---|
| Cyclomethicone | 2.00 |
| Ctyldimethicone copolyol | 0.20 |
| PEG 22-dodecyl copolymer | 3.00 |
| Paraffin oil (GP 9) | 2.00 |
| Caprylic acid/capric acid triglyceride | 5.80 |
| Octyl methoxycinnamate | 5.80 |
| Butylmethoxydibenzoylmethane | 4.00 |
| Salicin | 0.50 |
| α-tocopherol acetate | 0.50 |
| $ZnSO_4$ | 0.70 |
| $Na_4EDTA$ | 0.30 |
| Preservative, colorants, perfume | q.s. |
| Water | to 100.00 |

Example 10

| Sunscreen emulsion | % by weight |
|---|---|
| Cyclomethicone | 2.00 |
| Cetylstearyl alcohol + PEG 40 hydrogenated castor oil + sodium cetylstearyl sulphate | 2.50 |
| Glyceryl lanolate | 1.00 |
| Caprylic acid/capric acid triglyceride | 0.10 |
| Laurylmethicone copolyol | 2.00 |
| Octyl stearate | 3.00 |
| Castor oil | 4.00 |
| Glycerol | 3.00 |
| Acrylamide/sodium acrylate copolymer | 0.30 |
| Hydroxypropylmethylcellulose | 0.30 |
| Octyl methoxycinnamate | 5.00 |
| Butylmethoxydibenzoylmethane | 0.50 |
| Salicin | 0.50 |
| α-tocopherol acetate | 1.00 |
| $Na_3HEDTA$ | 1.50 |
| Preservative, colorants, perfume | q.s. |
| Water | to 100.00 |

Example 11

| Sunscreen emulsion | % by weight |
|---|---|
| Cyclomethicone | 2.00 |
| Cetylstearyl alcohol + PEG 40 hydrogenated castor oil + sodium cetylstearyl sulphate | 2.50 |
| Glyceryl lanolate | 1.00 |
| Caprylic acid/capric acid triglyceride | 0.10 |
| Laurylmethicone copolyol | 2.00 |
| Octyl stearate | 3.00 |
| Castor oil | 4.00 |
| Glycerol | 3.00 |
| Acrylamide/sodium acrylate copolymer | 0.30 |
| Hydroxypropylmethylcellulose | 0.30 |
| Octyl methoxycinnamate | 5.00 |
| Butylmethoxydibenzoylmethane | 0.75 |
| Salicin | 0.50 |
| $Na_3HEDTA$ | 1.50 |
| Preservative, colorants, perfume | q.s. |
| Water | to 100.00 |

Example 12

| Massage cream | % by weight |
|---|---|
| Stearyl alcohol | 2.00 |
| Petrolatum | 4.00 |
| Dimethicone | 2.00 |
| Isopropyl palmitate | 6.00 |
| Cetylstearyl alcohol | 4.00 |
| PEG hydrogenated castor oil | 2.00 |
| α-tocopherol | 0.50 |
| Salicin | 0.50 |
| Glycerol | 3.00 |
| Preservative, colorants, perfume | q.s. |
| Water | to 100.00 |

Example 13

| Hair lotion | % by weight |
|---|---|
| Ethanol | 40.00 |
| Diisopropyl adipate | 0.10 |
| PEG 40 hydrogenated castor oil | 0.20 |
| Salicin | 0.50 |
| α-tocopheryl acetate | 0.10 |
| Preservative, colorants, perfume | q.s. |
| Water | to 100.00 |

-continued

| Example 14 | |
|---|---|
| Spray formulation | % by weight |
| α-tocopherol | 0.10 |
| Salicin | 0.50 |
| Ethanol | 28.20 |
| Preservative, colorants, perfume | q.s. |
| Propane/butane 25/75 | to 100.00 |

We claim:

1. A method for the cosmetic or dermatological treatment and/or prophylaxis of irritant and/or erythematous skin symptoms which comprises applying as active ingredient an amount effective therefor of salicin.

2. A method according to claim 1, for the control and prophylaxis of the erythematous skin symptoms in the case of blemished skin or Acne vulgaris, wherein an amount of salicin effective therefor is applied to the skin.

3. A method according to claim 1, for the control and prophylaxis of the erythematous skin symptoms in the case of inflamed comedones, wherein an amount of salicin effective therefor is applied to the skin.

4. A method according to claim 1, for the control and prophylaxis of the erythematous skin symptoms in the case of reddened skin of infants in the diaper area, wherein an amount of salicin effective therefor is applied to the skin.

5. A method according to claim 1, for the control and prophylaxis of the erythematous skin symptoms in the case of inflamed skin around the mouth/nose area, wherein an amount of salicin effective therefor is applied to the skin.

6. A method according to claim 1, for the control and prophylaxis of the erythematous skin symptoms in the case of herpes labialis, wherein an amount of salicin effective therefor is applied to the skin.

7. A method according to claim 1, for the control and prophylaxis of the erythematous skin symptoms in the case of sunburn, wherein an amount of salicin effective therefor is applied to the skin.

8. A method according to claim 1, for the control and prophylaxis of the erythematous skin symptoms in the case of slight skin fissures, wherein an amount of salicin effective therefor is applied to the skin.

9. A method according to claim 1 for the control and prophylaxis of "stinging", wherein an amount of salicin effective therefor is applied to the skin.

10. A method according to claim 1 for the treatment of atopic dermatitis and skin allergies of type I and II, wherein an amount of salicin effective therefor is applied to the skin.

11. A method according to claim 1 for increasing the irritancy threshold in sensitive skin, wherein an amount of salicin effective therefor is applied to the skin.

12. A method according to claim 1, wherein the salicin is present in cosmetic or topical dermatological preparations in concentrations of 0.01–10% by weight based on the total weight of the preparations.

13. A method according to claim 1, wherein the salicin is present in cosmetic or topical dermatological preparations in concentrations of 0.1–5% by weight based on the total weight of the preparations.

14. A method according to claim 1, wherein the salicin is present in cosmetic or topical dermatological preparations in concentrations of 0.2–2.0% by weight based on the total weight of the preparations.

* * * * *